(12) United States Patent
Abe (10) Patent No.: US 9,188,773 B2
(45) Date of Patent: Nov. 17, 2015

(54) ENDOSCOPE

(71) Applicant: OLYMPUS CORPORATION, Tokyo (JP)

(72) Inventor: Masanao Abe, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 106 days.

(21) Appl. No.: 13/646,221

(22) Filed: Oct. 5, 2012

(65) Prior Publication Data

US 2013/0035549 A1 Feb. 7, 2013

Related U.S. Application Data

(63) Continuation of application No. PCT/JP2011/058318, filed on Mar. 31, 2011.

(30) Foreign Application Priority Data

Apr. 5, 2010 (JP) .................................. 2010-087182

(51) Int. Cl.
*A61B 1/00* (2006.01)
*A61M 25/00* (2006.01)
*G02B 23/24* (2006.01)
*A61B 1/005* (2006.01)

(52) U.S. Cl.
CPC .......... *G02B 23/2476* (2013.01); *A61B 1/0011* (2013.01); *A61B 1/0055* (2013.01); *A61B 1/00078* (2013.01); *G02B 23/2492* (2013.01)

(58) Field of Classification Search
USPC .......................... 600/127–130, 133, 139–152; 604/523–528
See application file for complete search history.

(56) References Cited

U.S. PATENT DOCUMENTS

| 2004/0193013 A1 | 9/2004 | Iwasaka et al. |
| 2005/0075538 A1* | 4/2005 | Banik et al. .................... 600/141 |
| 2008/0154094 A1* | 6/2008 | Nakamura ..................... 600/129 |

FOREIGN PATENT DOCUMENTS

| JP | 62-114526 A | 5/1987 |
| JP | 2000-279374 A | 10/2000 |
| JP | 2000279374 A | * 10/2000 ............... A61B 1/00 |
| JP | 2002-034900 A | 2/2002 |

OTHER PUBLICATIONS

Extended Supplementary European Search Report dated Mar. 31, 2015 from related European Application No. 11 76 5790.8.

* cited by examiner

*Primary Examiner* — Ryan Henderson
(74) *Attorney, Agent, or Firm* — Scully, Scott, Murphy & Presser, P.C.

(57) ABSTRACT

An endoscope comprising, in a part of an insertion portion having flexibility, a bending portion formed by covering an outermost circumference with a covering rubber. Respective end portions of the covering rubber being tightly bound to a rigid portion near the bending portion with a thread and fixed by applying an adhesive. In at least one end portion of both fixed end portions of the covering rubber, hardness of at least a portion in a range from an end portion in a center portion side of a portion tightly bound with the thread to an end portion in a center portion side of a portion to which the adhesive is applied is set higher than hardness in a center portion of the covering rubber.

12 Claims, 8 Drawing Sheets

ENDOSCOPE

CROSS REFERENCE TO RELATED APPLICATION

This application is a continuation application of PCT/JP2011/058318 filed on Mar. 31, 2011 and claims benefit of Japanese Application No. 2010-087182 filed in Japan on Apr. 5, 2010, the entire contents of which are incorporated herein by this reference.

BACKGROUND OF THE INVENTION

1. Field of the Invention

The present invention relates to an endoscope including a bending portion in an insertion portion and, more particularly, to an endoscope in which an end portion of covering rubber forming an outermost circumference of the bending portion is fixed to a rigid portion near the end portion by bonding.

2. Description of the Related Art

As an endoscope for medical use inserted into a body, there are a rigid endoscope in which an insertion portion does not have flexibility and a flexible endoscope in which an insertion portion has flexibility. In recent year, not only the flexible endoscope but also some rigid endoscopes include a bending portion in an insertion portion.

Figure 1:
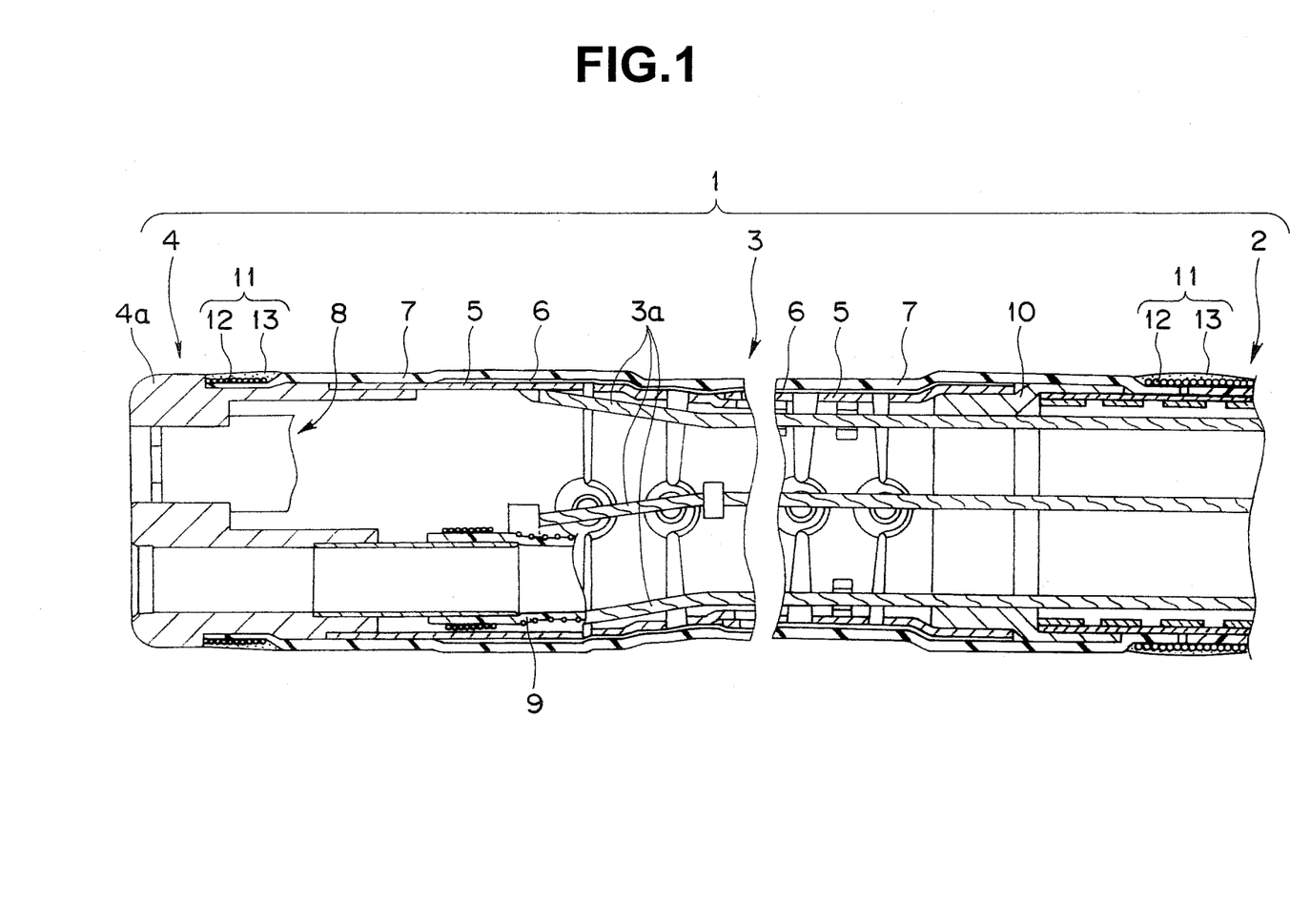
FIG. 1 is a diagram for explaining a schematic configuration of an insertion portion of an endoscope.

As shown in FIG. 1, an insertion portion 1 of a flexible endoscope is configured by consecutively connecting a flexible tube portion 2, a bending portion 3, and a distal end portion 4 including a distal end rigid portion 4a in order. The flexible tube portion 2 is elongated and has flexibility. The bending portion 3 is configured to bend, for example, in upward, downward, left, and right directions.

The bending portion 3 includes plural bending pieces 5, a net tube 6 that covers an outer circumference of the plural bending pieces 5, and covering rubber 7 that further covers an outer circumference of the net tube 6. The plural bending pieces 5 are pivotably consecutively connected. The covering rubber 7 is an outer skin tube that covers the net tube 6.

A not-shown image pickup apparatus included in an observation optical system 8 is provided at the distal end portion 4 of the insertion portion 1. In the insertion portion 1, a signal cable extending from an image pickup device provided in the image pickup apparatus, a not-shown light guide fiber bundle for transmitting illumination light, a channel tube for suction 9, a bending wire 3a used to perform bending operation of the bending portion 3, and the like are inserted.

Japanese Patent Application Laid-Open Publication No. 2002-34900 discloses that, for example, a distal end bending portion and a flexible tube portion of an insertion portion of an endoscope is usually covered with an outer skin tube having flexibility, an end portion of the outer skin tube needs to be fixed to a tubular member on an inner side to prevent liquid from intruding from the outside, it is difficult to obtain a sure fixed state simply by bonding the end portion of the outer skin tube to the tubular member on the inner side using an adhesive, or, in the past, a method of tightly binding the end portion of the outer skin tube with a silk thread or a nylon thread to firmly fix the end portion of the outer skin to the tubular member on the inner side and further applying the adhesive from an outer side to prevent loosening of the thread is adopted.

In the insertion portion 1 of the endoscope shown in FIG. 1, a thread reeling and bonding portion 11 for firmly fixing a distal end portion of the covering rubber 7 to the distal end rigid portion 4a and a thread reeling and bonding portion 11 for firmly fixing a proximal end portion of the covering rubber 7 to a coupling member 10 are provided. These thread reeling and bonding portions 11 include thread members 12 and adhesives 13. The thread members 12 tightly bind the covering rubber 7 to the distal end rigid portion 4a and tightly bind the covering rubber 7 to the coupling member 10. The adhesives 13 are applied around the tightly-bound thread members 12.

Figure 2:
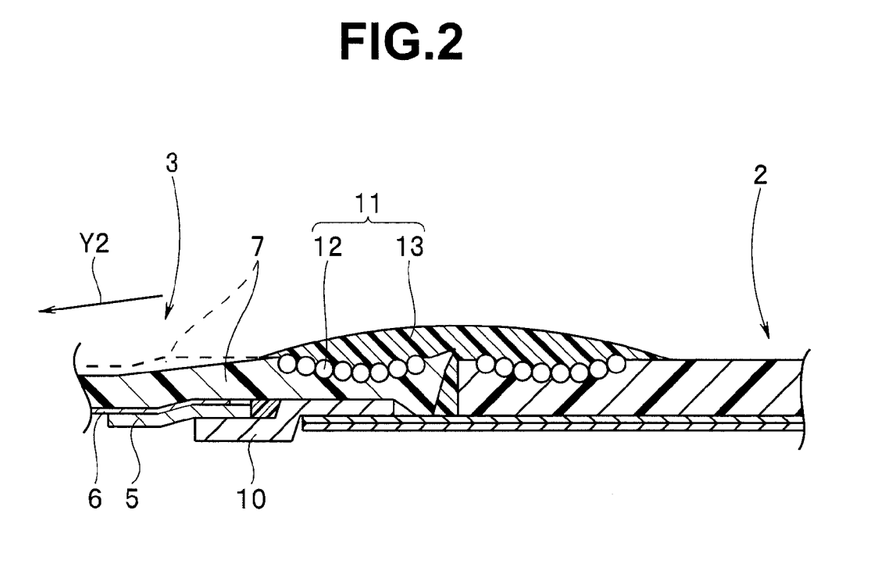
FIG. 2 is a diagram for explaining a tensile force applied to a covering rubber at the time of bending action of a bending portion.

However, in the insertion portion 1 of the endoscope, bending action of the bending portion 3 pulls the covering rubber 7 as indicated by an arrow Y2 in FIG. 2 and thickness of the insertion portion 1 decreases. When the bending action of the bending portion 3 is released, the pulled covering rubber 7 returns to an original state as indicated by a broken line.

In an endoscope for medical use, in recent years, high-temperature high-pressure steam sterilization has been adopted for disinfecting of the endoscope. When the endoscope is subjected to the high-temperature high-pressure steam sterilization, a waterproofing cap with a pressure regulating valve for adjusting pressure in a space on an inside of the endoscope is attached to an electric connector section of the endoscope. An endoscope including the same pressure regulating valve in a vent hole of a connector section of the endoscope is subjected to the high-temperature high-pressure steam sterilization without the waterproofing cap being attached to the endoscope.

Sterilization treatment by high-temperature high-pressure steam for the endoscope is performed in the order of a pre-process, a sterilization process, and a drying process. In the pre-process, pressure in a sterilization room is reduced and pressure on an outside of the endoscope is lower than an inside of the endoscope. Then, the pressure regulating valve of the waterproofing cap opens to allow the inside and the outside of the endoscope to communicate with each other. As a result, for example, a deficiency due to expansion caused by a large pressure difference between inner pressure of the endoscope and pressure in the sterilization room is prevented. In the pre-process, decompression is repeatedly performed at a predetermined time interval. Therefore, during the decompression, the covering rubber 7 expands, although a little. When the decompression is released, the covering rubber 7 is pulled to an inner side of the endoscope.

In the sterilization process, an inside of the sterilization room is pressurized, whereby pressure on the outside of the endoscope is higher than pressure on the inside of the endoscope. At this point, the pressure regulating valve is closed. The covering rubber 7 is pressurized as indicated by an arrow Y3 in FIG. 3 to thereby be crushed as indicated by a solid line from the state indicated by the broken line.

Figure 3:
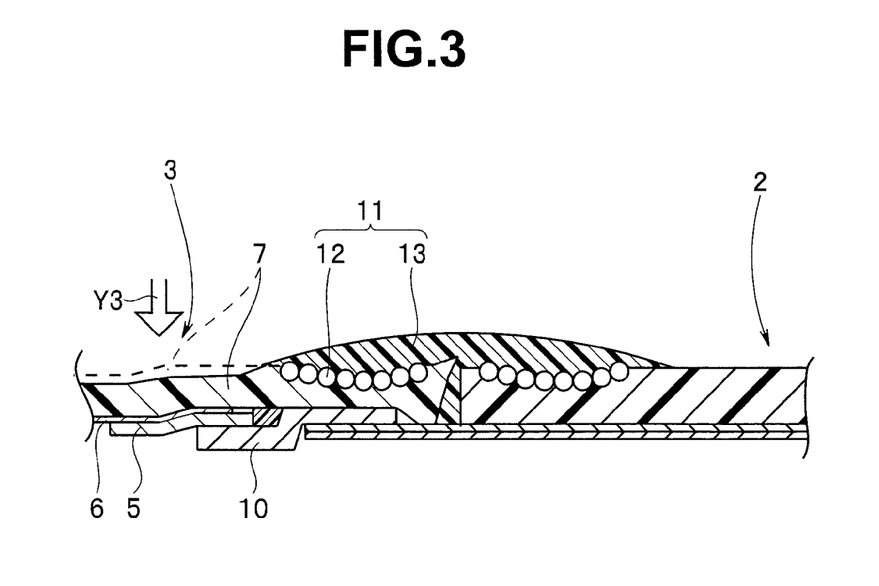
FIG. 3 is a diagram for explaining a state in which the covering rubber is crushed by pressurization when the endoscope is subjected to high-temperature high-pressure steam sterilization.

Thereafter, in the drying process, decompression is repeated as in the pre-process. As a result, the covering rubber 7 repeats deformation.

Figure 4:
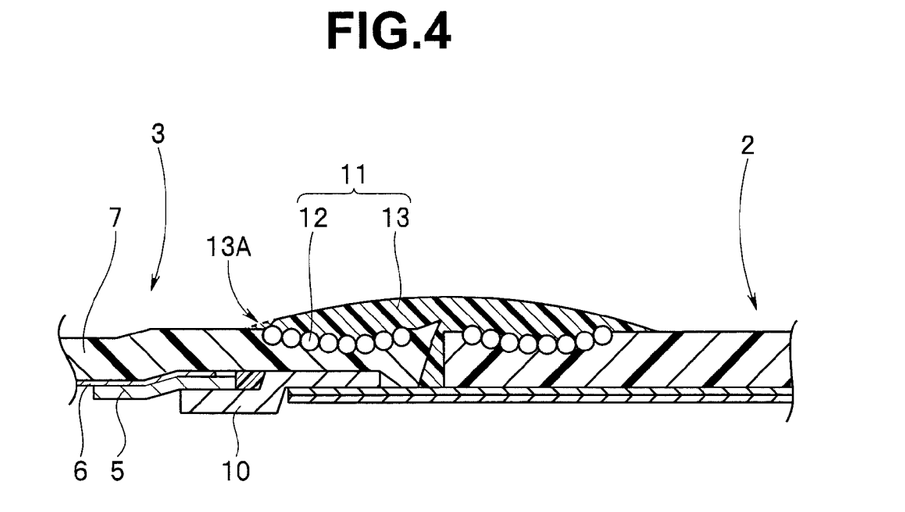
FIG. 4 is a diagram for explaining peeling of an adhesive for fixing the covering rubber.

In this way, the covering rubber 7 is deformed in the bending action or in the high-temperature high-pressure steam sterilization. When the covering rubber 7 is deformed, a load is applied to an interface between the covering rubber 7 and the adhesive 13. It is likely that an end portion 13A of the adhesive 13, which fixes the covering rubber 7, peels as shown in FIG. 4.

As representative high-temperature high-pressure steam sterilization treatment, there is, for example, United States Standard ANSI/AAMI ST-79 issued by the Medical Equipment Development Association approved by the United States Standard Association. As specific conditions, it is specified that the treatment is performed for four minutes at 132° C. in the sterilization process including the pre-process.

SUMMARY OF THE INVENTION

An endoscope according to an aspect of the present invention comprising, in a part of an insertion portion having flexibility, a bending portion formed by covering an outermost circumference with a covering rubber, respective end portions of the covering rubber being tightly bound to a rigid portion near the bending portion with a thread and fixed by applying an adhesive, wherein in at least one end portion of both fixed end portions of the covering rubber, hardness of at least a portion in a range from an end portion in a center portion side of a portion tightly bound with the thread to an end portion in a center portion side of a portion to which the adhesive is applied is set higher than hardness in a center portion of the covering rubber.

BRIEF DESCRIPTION OF THE DRAWINGS

FIGS. 1 to 4 relate to a configuration example in the past, wherein

DETAILED DESCRIPTION OF THE PREFERRED EMBODIMENT

An embodiment of the present invention is explained in detail below with reference to the drawings.

The embodiment of the present invention is explained below with reference to FIGS. 5 to 9.

Figure 5:
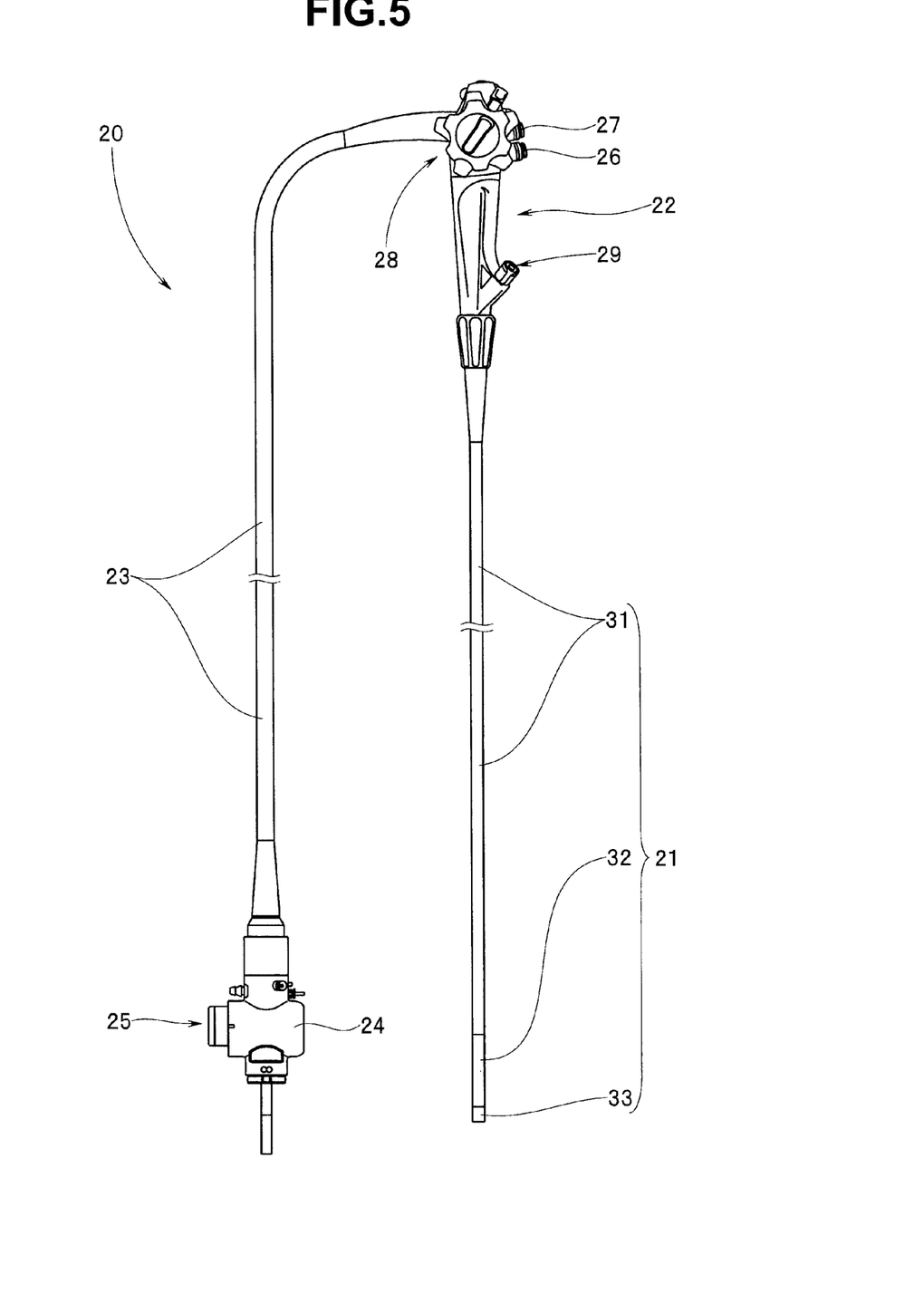
FIG. 5 is a diagram for explaining a configuration of the endoscope.

As shown in FIG. 5, an endoscope 20 includes an insertion portion 21, an operation section 22, and a universal cord 23. The insertion portion 21 is elongated and has flexibility. The operation section 22 is provided on a proximal end side of the insertion portion 21. The universal cord 23 has flexibility and extends from a side portion of the operation section 22.

An endoscope connector 24 detachably connected to a light source apparatus (not shown), which is an outside apparatus, is provided at an end portion of the universal cord 23. An electric connector section 25 is provided on a side portion of the endoscope connector 24. A signal cable (not shown) detachably attachable to a video processor (not shown), which is an outside apparatus, is connected to the electric connector section 25. A waterproofing cap (not shown) with a pressure regulating valve is attached to the electric connector section 25 when high-temperature high-pressure steam sterilization is performed.

An air-supply and water-supply button 26, a suction button 27, a bending operation knob 28, a treatment instrument insert-through pipe sleeve 29, and the like are provided in the operation section 22.

The insertion portion 21 is configured by consecutively connecting a flexible tube portion 31, a bending portion 32, and a distal end portion 33. The flexible tube portion 31 has flexibility. The bending portion 32 is provided on a distal end side of the flexible tube portion 31. Bending action of the bending portion 32 is caused according to operation of the bending operation knob 28. The distal end portion 33 is provided on a distal end side of the bending portion 32. An observation optical system, an illumination optical system, and the like are provided at the distal end portion 33.

Figure 6:
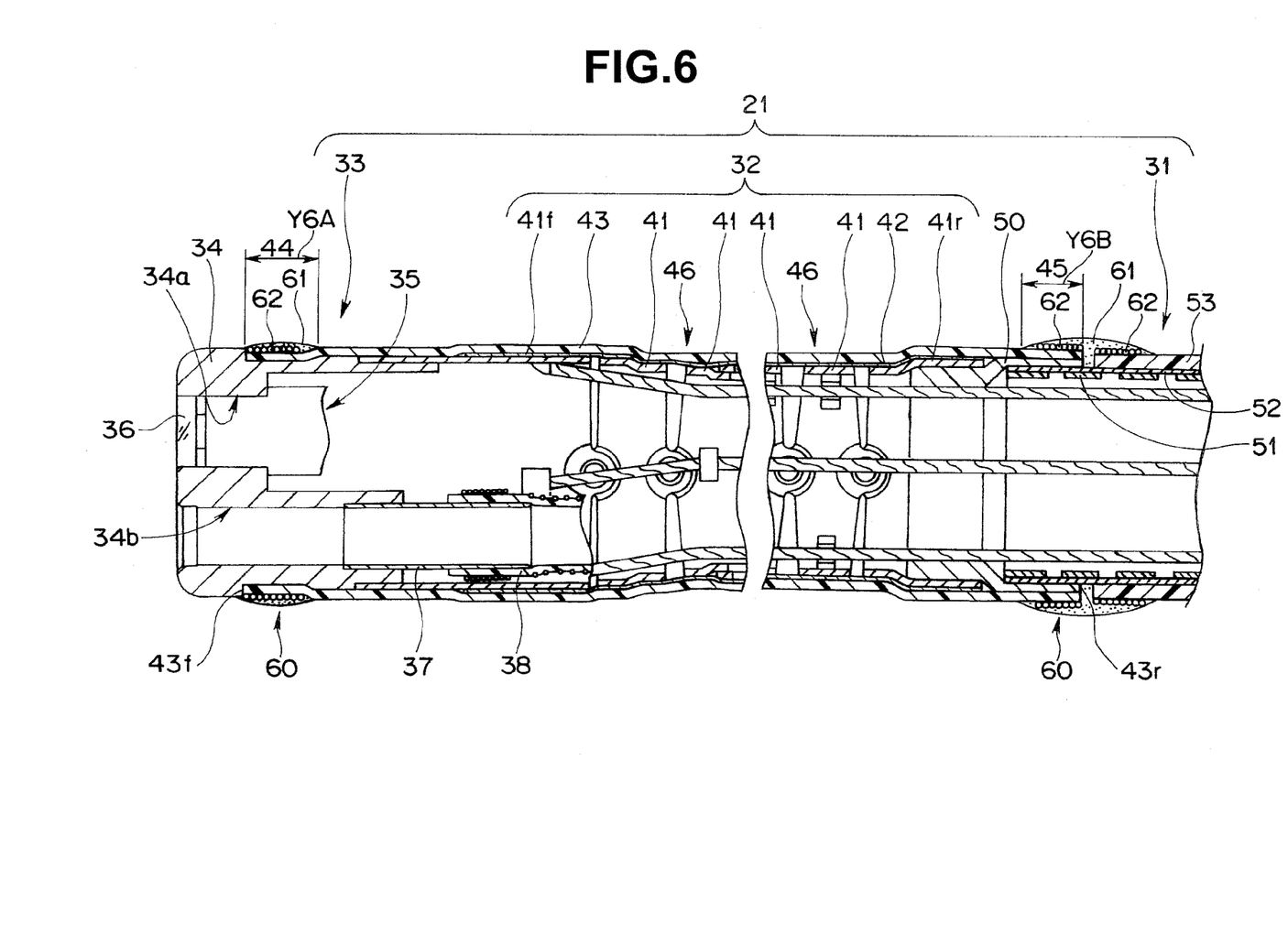
FIG. 6 is a diagram for explaining a configuration of the bending portion included in the insertion portion and a periphery of the bending portion.

As shown in FIG. 6, the distal end portion 33 includes a distal end rigid portion 34. For example, four through-holes parallel to a longitudinal axis are formed in the distal end rigid portion 34. An observation optical system 35 is disposed in a first through-hole 34a. An observation window 36 is fixedly provided on a distal end side of the first through-hole 34a. A second through-hole 34b is a suction port. The second through-hole 34b communicates with, via a pipe sleeve 37, a channel tube for suction 38 also functioning as a channel tube for inserting through a treatment instrument. In the figure, an illumination optical system is disposed in a not-shown third through-hole. An air-supply and water-supply nozzle is disposed in a fourth through-hole.

The number of through-holes is not limited to four and may be equal to or larger than or equal to or smaller than four. The through-holes include at least a through-hole in which an observation optical system is disposed and a through-hole in which an illumination optical system is disposed.

The bending portion 32 includes plural bending pieces 41, a net tube 42, and covering rubber 43. The net tube 42 is provided to cover the plural bending pieces 41. The covering rubber 43 covers a further outer circumference of the net tube 42. The plural bending pieces 41 are pivotably consecutively connected to bend, for example, in upward, downward, left, and right directions. The covering rubber 43 is an outer skin that forms an outermost circumference of the bending portion 32. A bending piece located at a most distal end of the bending portion 32 among the plural bending pieces 41 is a distal end bending piece 41f. A bending piece located at a rear most end is a rear end bending piece 41r.

The distal end bending piece 41f is integrally fixed to a proximal end side outer circumferential surface of the distal end rigid portion 34, which is a rigid portion, by, for example, an adhesive. On the other hand, the rear end bending piece 41r is integrally fixed to a distal end side outer circumferential surface of a coupling pipe sleeve 50, which is a rigid portion provided on a distal end side of the flexible tube portion 23, by, for example, an adhesive.

The covering rubber 43 is made of, for example, fluorocarbon rubber. In the covering rubber 43, hardness of a distal end side end portion 44 in a range indicated by an arrow Y6A, hardness of a rear end side end portion 45 in a range indicated by an arrow Y6B, and hardness of a center portion 46 located between the distal end side end portion 44 and the rear end side end portion 45 are different.

Specifically, end portion hardness of the distal end side end portion 44 and the rear end side end portion 45 of the covering rubber 43 is rubber hardness A90 when represented in JIS K 6253 (durometer). On the other hand, center hardness of the center portion 46 is rubber hardness A60. The end portion hardness is set higher than the center hardness. Setting the center portion 46 to the rubber hardness A60 allows for smooth bending action of the bending portion 32.

The covering rubber 43, in which the end portion hardness of the distal end side end portion 44 and the rear end side end portion 45 and the center hardness of the center portion 46 are different, is manufactured by a manufacturing method explained in (1) to (3) below.

(1) Both end portions of a rubber member having the hardness A60 are respectively immersed in cross-linking reagents to raise cross-linking density of both end portions 44 and 45 of the rubber member. As a result, the covering rubber 43 is obtained in which the hardness of both end portions 44 and 45 having the rubber hardness A90 having the rubber hardness A60 is higher than the hardness of the center portion 46.

(2) Thermoplastic elastomers having different hardnesses are mixed and a mixing amount is changed in the longitudinal direction to manufacture the covering rubber 43. In manufacturing the covering rubber 43, the hardnesses of both end portions 44 and 45 and the center portion 46 of the covering rubber are changed and the hardness of both end portions 44 and 45 is set to the rubber hardness A90 higher than the hardness of the center portion 46.

Figure 7:
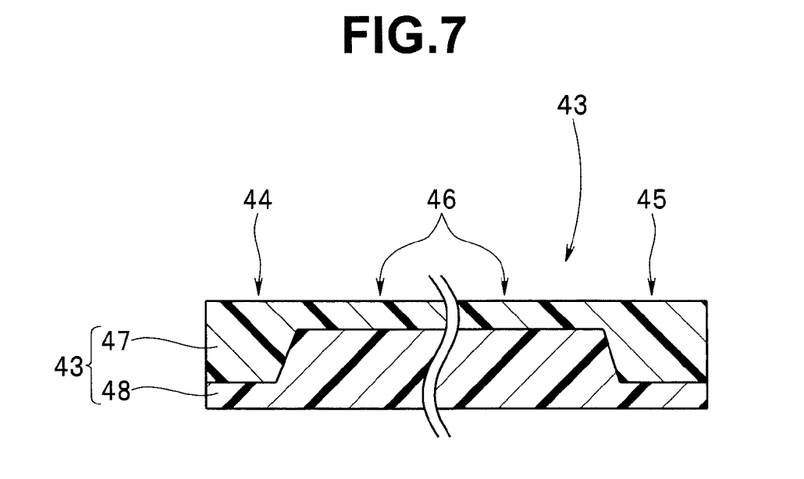
FIG. 7 is a diagram for explaining covering rubber formed by multi-layering thermoplastic elastomers having different hardnesses in a longitudinal direction.

(3) The covering rubber 43 shown in FIG. 7 is manufactured by laminating thermoplastic elastomers (simply described as elastomers) 47 and 48 having different hardnesses. A ratio of thickness in the longitudinal direction of the first elastomer 47 and a ratio of thickness in the longitudinal direction of the second elastomer 48 are changed to set the hardness of both end portions 44 and 45 of the covering rubber 43 to the rubber hardness A90 higher than the hardness of the center portion 46.

The hardness of the first elastomer 47 is higher than the hardness of the second elastomer 48.

In the manufacturing method explained above, the hard first elastomer is used in an outer layer and the soft second elastomer is used in an inner layer. However, the covering rubber 43 is not limited to the configuration for hardening the outer layer and softening the inner layer and may be an opposite configuration. The covering rubber 43 may include three or more layers of thermoplastic elastomers.

Figure 8:
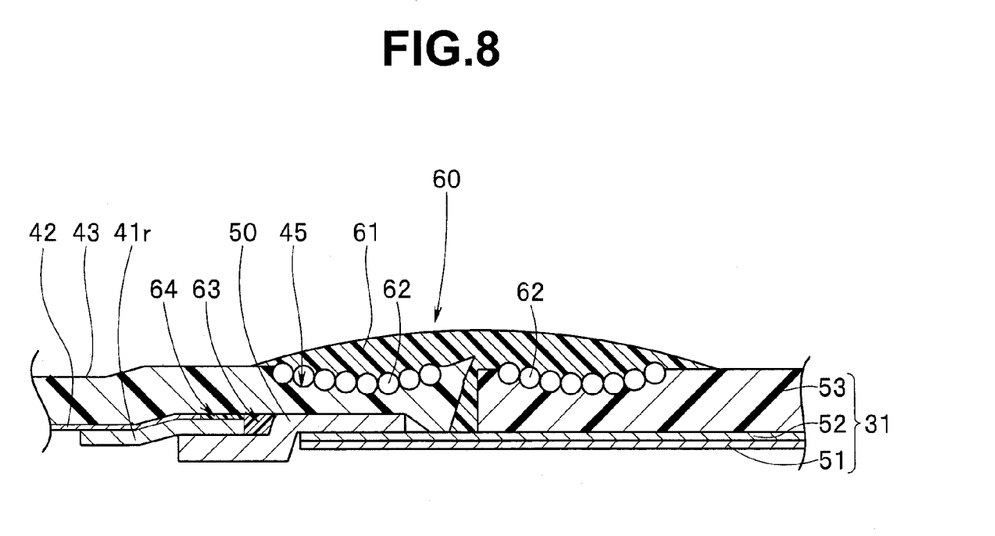
FIG. 8 is a diagram for explaining a configuration on a rear end side of the bending portion.

The covering rubber 43 in the present embodiment includes the distal end side end portion 44 and the rear end side end portion 45 having the rubber hardness A90. As shown in FIGS. 6 and 8, the distal end side end portion 44 of the covering rubber 43 is arranged to be externally fit in a proximal end side of the distal end rigid portion 34. The distal end side end portion 44 is bonded and fixed to the distal end rigid portion 34 by heaping up an adhesive 61. On the other hand, the rear end side end portion 45 of the covering rubber 43 is arranged to be externally fit in the coupling pipe sleeve 50 and bonded and fixed to the coupling pipe sleeve 50 by heaping up the adhesive 61.

In the present embodiment, a bonded portion 60 formed by solidifying the adhesive 61 is provided on the distal end side end portion 44 and the proximal end side end portion 45.

The hardness of the distal end side end portion 44 and the proximal end side end portion 45 is not limited to the rubber hardness A90 and is set in a range of rubber hardness A70 to rubber hardness D70.

The flexible tube portion 23 includes a spiral tube 51, a net tube 52, and outer skin resin 53. The spiral tube 51 is obtained by winding a belt-like plate member made of metal or the like in spiral shape. The net tube 52 is sheathed over the spiral tube 51. The net tube 52 is formed by weaving an element wire made of a polymeric material, metal, or the like in a tubular shape. The outer skin resin 53 covers an outer circumference of the net tube 52.

In the present embodiment, after the distal end side end portion 44 is tightly bound to the distal end rigid portion 34 by a thread 62, the bonding and fixing by the adhesive 61 is performed to more surely bond and fix the distal end side end portion 44 to the distal end rigid portion 34. After the rear end side end portion 45 is tightly bound to the coupling pipe sleeve 50 by the thread 62, the bonding and fixing by the adhesive 61 is performed to more surely bond and fix the rear end side end portion 45 to the coupling pipe sleeve 50.

As the tightly binding thread, a thread is used that is obtained by binding, weaving, or twisting at least one kind of fiber selected out of a group including aramid fiber, polyarylate fiber, poly-phenylene-benzobisoxazole, and carbon fiber, which is not dissolved, hydrolyzed, contracted, or permanently deformed by steam used for sterilization after use of the endoscope, has breaking elongation within 10%, is not thermally deformed, and has a melting point or a decomposition temperature equal to or higher than 300° C.

In the present embodiment, in order to suppress crush of the covering rubber 43 during pressurization of the high-temperature high-pressure steam sterilization, an adhesive is applied to a surface of the distal end rigid portion 34, which is a rigid portion to which an end portion of the covering rubber 43 is arranged to be externally fit, and a surface of the coupling pipe sleeve 50 to form the surfaces as smooth surfaces. Specifically, the adhesive is filled in a gap portion 63 between the rear end bending piece 41r and the coupling pipe sleeve 50 shown in FIG. 8 for example and a recess of, for example, a surface 64 of the bending piece 41r, to which an end portion of the net tube 42 is joined, to form smooth surfaces.

The endoscope 20 including the insertion portion 21, in which the outermost circumference of the bending portion 32 was formed of covering rubber 43 manufactured by any one of the manufacturing methods (1) to (3), and an endoscope including the insertion portion 1, in which the outermost circumference of the bending portion 3 was formed of the covering rubber 7, were manufactured. A change in a bending force amount that occurred when the bending operation knob is bend-operated to bend the bending portions 3 and 32 into a state set in advance and a change in a state of a bonded portion after the high-temperature high-pressure steam sterilization were compared. One hundred examples of a tolerance test of the high-temperature high-pressure steam sterilization were performed.

Test conditions for the high-temperature high-pressure steam sterilization are shown in Table 1 below.

TABLE 1

| Process name | Detailed conditions (pressure is gauge pressure) |
| --- | --- |
| Sterilization process | 136° C./18 minutes (220 kPa) |
| Pre-process (decompression process 1) | Pulse type decompression three times (−85 kPa) |
| Drying process (decompression process 2) | Pulse type for 30 minutes (−85 kPa) |

A result of the test is shown in Table 2 below.

TABLE 2

| Type of covering rubber | State of bonded portion | Bending force amount |
| --- | --- | --- |
| Covering rubber 7 | Bonded portion peels in thirtieth example | Within specified range |
| Covering rubber 43 manufactured by (1) | No change in bonded portion | Within specified range |
| Covering rubber 43 manufactured by (2) | No change in bonded portion | Within specified range |
| Covering rubber 43 manufactured by (3) | No change in bonded portion | Within specified range |

Figure 9:
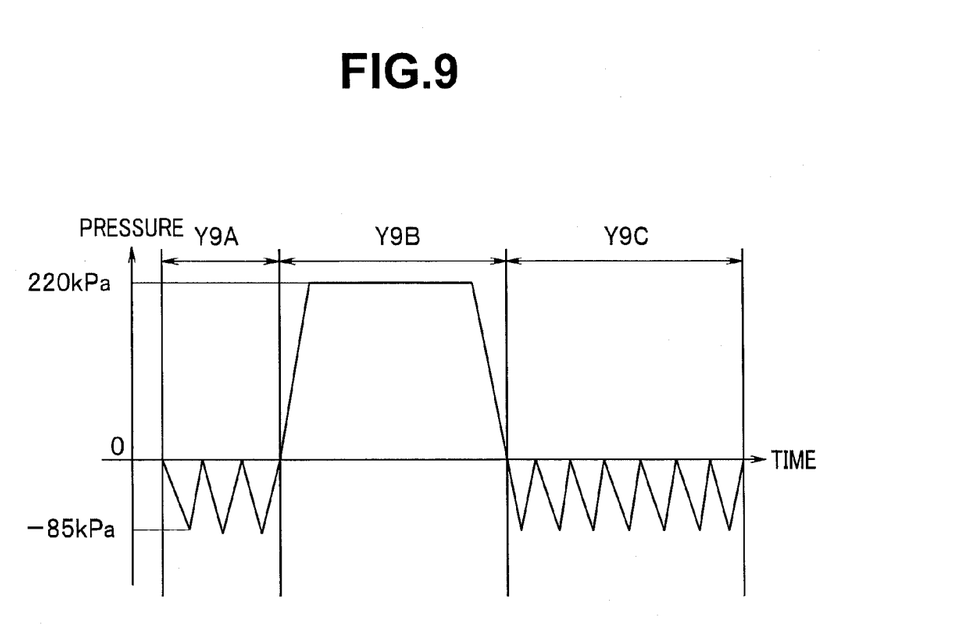
FIG. 9 is a diagram for explaining a relation between time and pressure during the high-temperature high-pressure steam sterilization.

FIG. 9 is a diagram for explaining a relation between time and pressure during the high-temperature high-pressure steam sterilization. A range indicated by an arrow Y9A is a pre-process. A range indicated by an arrow Y9B is a sterilization process. A range indicated by an arrow Y9C is a drying process.

Bending action of the bending portion 32 of the endoscope 20 is caused by the operation of the bending operation knob 28. Since the hardness of the center portion 46 of the covering rubber 43 is set to the rubber hardness A60, bending is possible with a predetermined bending force amount. In the endoscope 20, when the covering rubber 43 is pulled by bending action of the bending portion 32, since the hardness of both end portions 44 and 45 of the covering rubber 43 is set to the rubber hardness A90, a change in the thickness at both end portions 44 and 45 is little. As a result, a load applied to an interface between both end portions 44 and 45 of the covering rubber 43 and the bonded portion 60 decreases.

Sterilization treatment by high-temperature high-pressure steam of the endoscope 20 is performed in the order of the pre-process, the sterilization process, and the drying process as shown in FIG. 9.

In the pre-process, pressure in a sterilization room is reduced. In the pre-process, decompression and decompression release are repeatedly performed, for example, three times. Since the decompression and the decompression release are repeated, expansion and contraction of the covering rubber 43 are repeated. In the present embodiment, both end portions 44 and 45 of the covering rubber 43 are set to the rubber hardness A90. Therefore, when the expansion and the contraction of the covering rubber 43 are repeated, the load applied to the interface between both end portions 44 and 45 of the covering rubber 43 and the bonded portion 60 decreases.

In the sterilization process, an inside of the sterilization room is pressurized and pressure on an outside of the endoscope becomes higher than pressure on an inside of the endoscope. At this point, since the end portion hardness of both end portions 44 and 45 of the covering rubber 43 is set to the rubber hardness A90, the crush due to pressurization decreases. As a result, the load applied to the interface between both end portions 44 and 45 of the covering rubber 43 and the bonded portion 60 decreases.

Thereafter, in the drying process, decompression is repeated as in the pre-process. In the drying process, as in the pre-process and the sterilization process, since both end portions 44 and 45 of the covering rubber 43 is set to the rubber hardness A90, the load applied to the interface between both end portions 44 and 45 and the bonded portion 60 decreases as in the configuration explained above.

In this way, the end portion hardness of the distal end side end portion 44 and the end portion hardness of the rear end side end portion 45 of the covering rubber 43 included in the bending portion 32 of the insertion portion 21 are set to the rubber hardness A90 higher than the center hardness of the center portion 46. As a result, the load applied to the interface between both end portions 44 and 45 of the covering rubber 43 and the bonded portion 60 can be reduced.

Consequently, the adhesive 61 for fixing the covering rubber 43 is prevented from peeling because of the repeatedly-performed bending actions and the repeatedly-performed high-temperature high-pressure steam sterilization.

In the embodiment explained above, both of the end portion hardness of the distal end side end portion 44 and the end portion hardness of the rear end side end portion 45 of the covering rubber 43 are set to the rubber hardness A90. However, a level of tolerance is slightly different between a distal end side and a rear end side of the distal end side end portion or the rear end side end portion. For example, the crush of the covering rubber during the sterilization process can also be reduced by setting an outer diameter of one of the distal end rigid portion 34, which is the rigid portion, and the coupling pipe sleeve 50 large and deforming the covering rubber 43 to be thin in advance. In this case, only one end portion of the covering rubber 43 may be set to the rubber hardness A90.

In the embodiment explained above, the bonded portion 60 is provided on the distal end side end portion 44 and the rear end side end portion 45 set to the rubber hardness A90. However, the portion where the covering rubber 43 is deformed in advance is not limited to the distal end side end portion 44 and the rear end side end portion 45 set to the rubber hardness A90 and may be formed as shown in FIG. 10 or as shown in FIG. 11.

Figure 10:
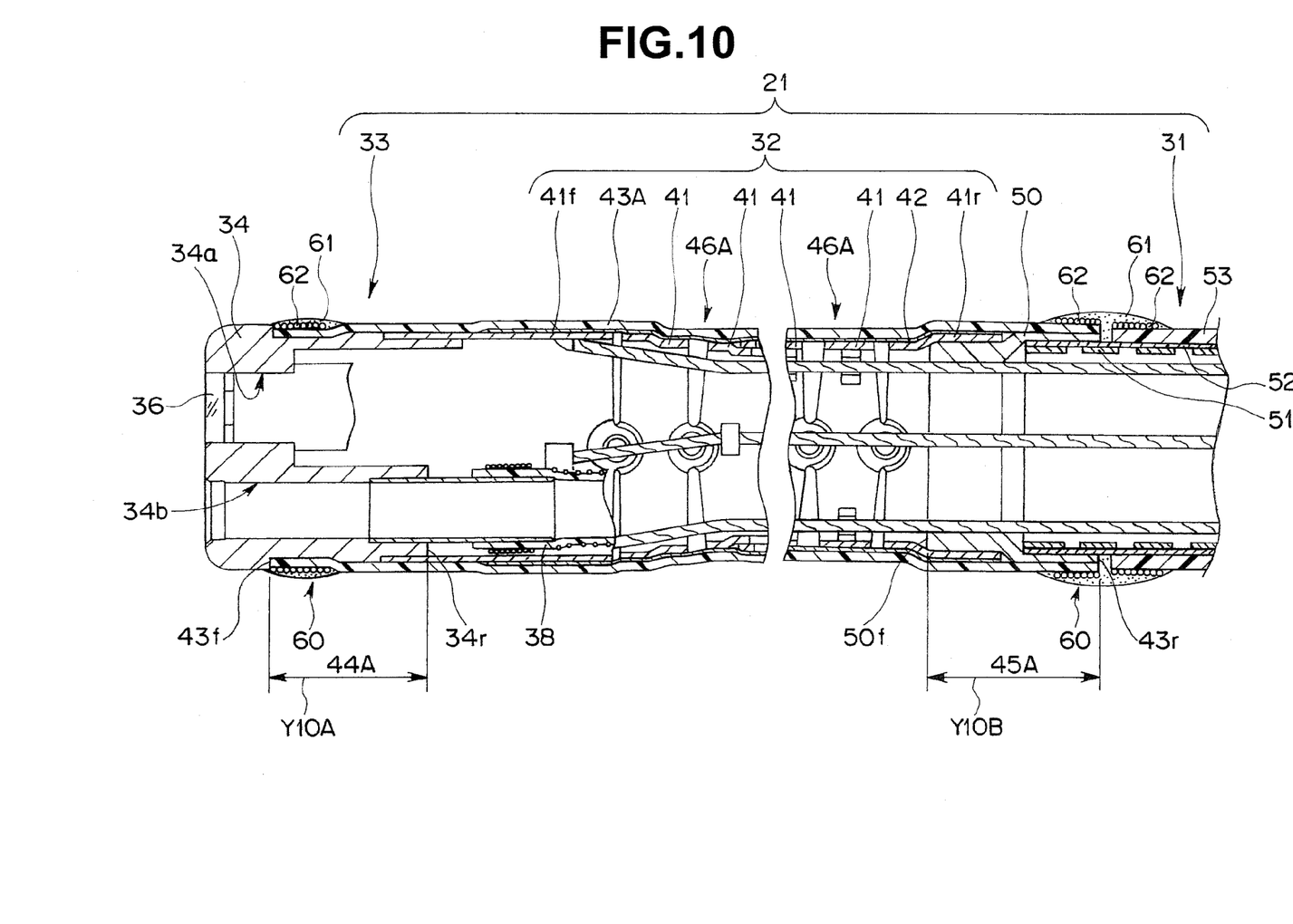
FIG. 10 is a diagram for explaining another configuration of the bending portion included in the insertion portion and the periphery of the bending portion.
Figure 11:
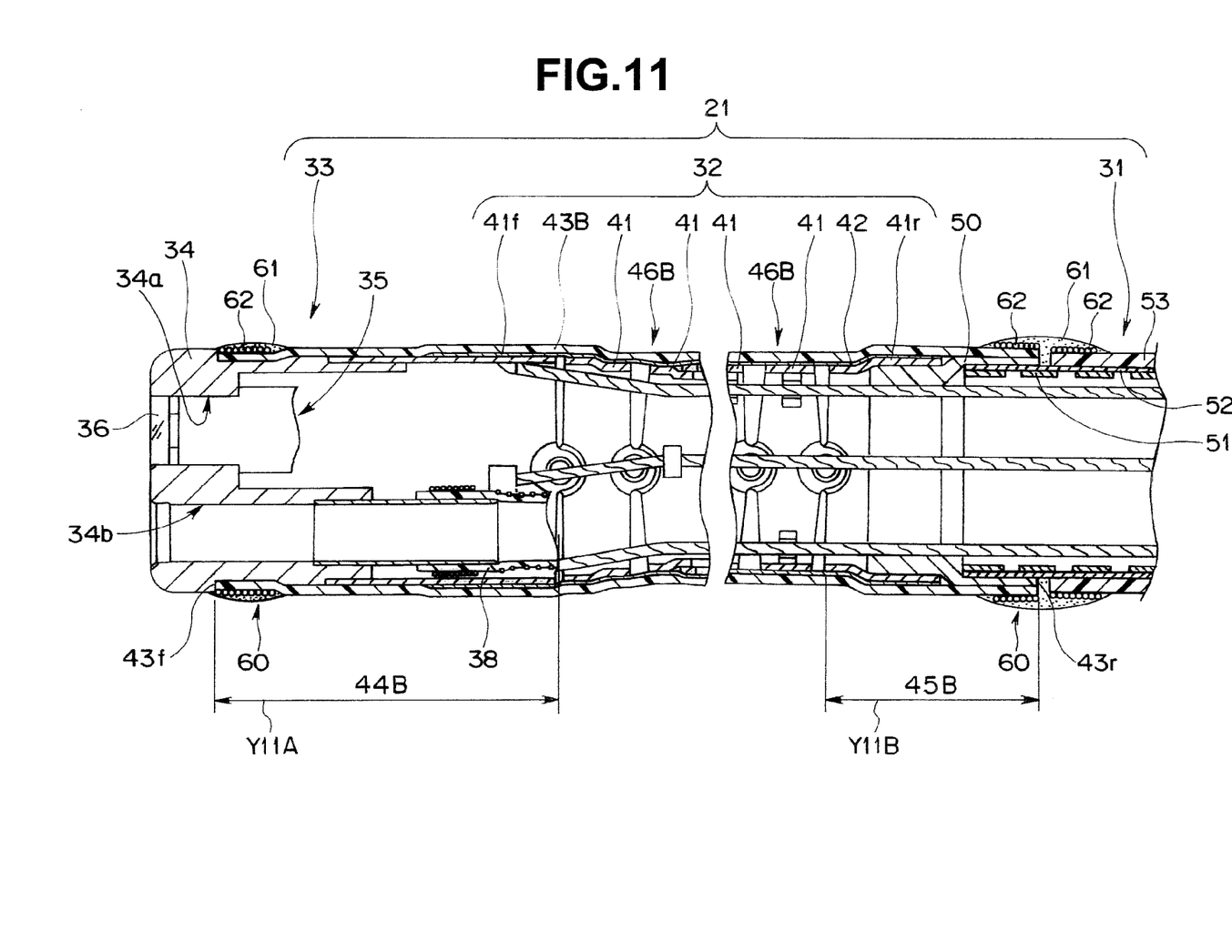
FIG. 11 is a diagram for explaining still another configuration of the bending portion included in the insertion portion and the periphery of the bending portion.

In a covering rubber 43A shown in FIG. 10, for example, end portion hardness of a distal end side end portion 44A in a range indicated by an arrow Y10A and end portion hardness of a rear end side end portion 45A in a range indicated by an arrow Y10B are set to the rubber hardness A90 higher than the center hardness of the center portion 46.

The distal end side end portion 44A of the covering rubber 43A is set to be arranged from a rubber distal end face 43*f* to an outer circumferential surface or a proximal end face 34*r* of the distal end rigid portion 34, i.e., arranged on the outer circumferential surface of the distal end rigid portion 34. On the other hand, the rear end side end portion 45A is set to be arranged from a rubber proximal end face 43*r* to an outer circumferential surface or a distal end face 50*f* of the coupling pipe sleeve 50, i.e., arranged on the outer circumference of the coupling pipe sleeve 50.

In the present embodiment, the bonded portion 60 of the distal end side end portion 44A is provided from the rubber distal end face 43*f* to a halfway part of the distal end side end portion 44A at a distance set in advance. On the other hand, the bonded portion 60 of the rear end side end portion 45A is provided from the rubber rear end face 43*r* to a halfway part of the rear end side end portion 45A at a distance set in advance.

With this configuration, the distal end side end portion 44A set to the rubber hardness A90 is arranged on the outer circumferential surface of the distal end rigid portion 34 and the rear end side end portion 45A is arranged on the outer circumferential surface of the coupling pipe sleeve 50. As a result, the covering rubber 43A can prevent an operation force amount for bending the bending portion 32 from increasing.

The bonded portions 60 are respectively provided between the end face and the halfway part of the distal end side end portion 44A set to the rubber hardness A90 and between the end face and the halfway part of the rear end side end portion 45A. As a result, the covering rubber 43A can surely prevent vicinities of the bonded portions 60 from being deformed by tension during the bending action of the bending portion 32 and prevent the vicinities of the bonded portions 60 from being deformed by pressurization during the high-temperature high-pressure steam sterilization. Therefore, the adhesive 61 for fixing the covering rubber 43A can be prevented from peeling because of deformation of the covering rubber around the adhesive 61.

In a covering rubber 43B shown in FIG. 11, end portion hardness of a distal end side end portion 44B in a range indicated by an arrow Y11A and end portion hardness of a rear end side end portion 45B in a range indicated by an arrow Y11B are set to the rubber hardness A90 higher than the center hardness of the center portion 46.

The distal end side end portion 44B of the covering rubber 43B is set from a rubber distal end face 43f to a halfway part or a proximal end of the distal end bending piece 41f integrally fixed to the distal end rigid portion 34 and included in the rigid portion, i.e., set longer than the distal end side end portion 44A. On the other hand, the rear end side end portion 45B is set from a rubber proximal end face 43r to a halfway part or a distal end of the rear end bending piece 41r integrally fixed to the coupling pipe sleeve 50 and included in the rigid portion, i.e., set longer than the rear end side end portion 45A.

In the present embodiment, the bonded portion 60 of the distal end side end portion 44B is provided from the rubber distal end face 43f to a halfway part of the distal end side end portion 44B at a distance set in advance. On the other hand, the bonded portion 60 of the rear end side end portion 45B is provided from the rubber rear end face 43r to a halfway part of the rear end side end portion 45B at a distance set in advance.

With this configuration, the distal end side end portion 44B set to the rubber hardness A90 is arranged on the outer circumferential surface of the distal end rigid portion 34 and on an outer circumferential surface of the distal end bending piece 41f. The rear end side end portion 45B is arranged on the outer circumferential surface of the coupling pipe sleeve 50 and an outer circumferential surface of the rear end bending piece 41r. As a result, the covering rubber 43B can prevent an operation force amount for bending the bending portion 32 from increasing.

Lengths of the distal end side end portion 44B and the rear end side end portion 45B set to the rubber hardness A90 are respectively set larger than length of the distal end side end portion 44A and length of the rear end side end portion 45A. As a result, compared with the covering rubber 43A, the covering rubber 43B can more surely prevent the vicinities of the bonded portions 60 from being deformed by tension during the bending action and prevent the vicinities of the bonded portions 60 from being deformed by pressurization during the high-temperature high-pressure steam sterilization. Therefore, the adhesive 61 for fixing the covering rubber 43B can be more surely prevented from peeling because of deformation of the rubber around the adhesive 61.

The present invention is not limited to the embodiment explained above and can be carried out in various modifications without departing from the spirit of the invention.

What is claimed is:

1. An endoscope comprising:
   a bending portion provided in a part of an insertion portion having flexibility, wherein the bending portion comprises a plurality of joint rings;
   a covering rubber configured to cover an outer circumference of the joint rings of the bending portion and having a distal end and a proximal end,
      wherein the covering rubber is formed integrally by laminating a first thermoplastic elastomer and a second thermoplastic elastomer having different rubber hardness degrees,
      wherein each of the first thermoplastic elastomer and the second thermoplastic elastomer extend from the proximal end to the distal end of the covering rubber with a thickness of each of the first thermoplastic elastomer and the second thermoplastic elastomer changing along a longitudinal direction of the covering rubber such that rubber hardness degrees of a proximal end portion and a distal end portion of the covering rubber are greater than rubber hardness degrees of a center portion of the covering rubber, and
      wherein the covering rubber maintains a constant thickness from the proximal end to the distal end of the covering rubber;
   first and second tightly bound portions provided by tightly binding threads along outer circumferences of the distal end portion and the proximal end portion, respectively, of the covering rubber so as to fix the distal end portion and the proximal end portion to a first rigid portion and a second rigid portion, respectively, which are adjacent to the bending portion; and
   first and second bonded portions provided on outer circumferences of the first and second tightly bound portions, respectively, by applying adhesives from the first and second tightly bound portions so as to reach the distal end portion and the proximal end portion.

2. The endoscope according to claim 1,
   wherein the rubber hardness degrees of the distal end portion which has rubber hardness degrees greater than the rubber hardness degrees of the center portion of the covering rubber is arranged on an outer circumferential surface of the first rigid portion provided at a distal end of the insertion portion,
   wherein the proximal end portion which has rubber hardness degrees greater than the rubber hardness degrees of the center portion of the covering rubber is arranged on an outer circumferential surface of the second rigid portion provided at a distal end side of a flexible tube portion of the insertion portion,
   wherein the adhesive applied to the covering rubber and constituting the first bonded portion is applied from a halfway part of the first rigid portion to the distal end of the covering rubber, and
   wherein the adhesive applied to the covering rubber and constituting the second bonded portion is applied from a halfway part of the second rigid portion to the proximal end of the covering rubber.

3. The endoscope according to claim 1, wherein at least one of the distal end portion and the proximal end portion arranged on opposite sides of the center portion of the covering rubber has rubber hardness degrees in a range of rubber hardness degrees A70 to rubber hardness degrees D70.

4. The endoscope according to claim 1, wherein at least one of the distal end portion and the proximal end portion arranged on opposite sides of the center portion of the covering rubber has predetermined rubber hardness degrees greater than the rubber hardness degrees of the center portion to reduce loads applied to interfaces between the covering rubber and the adhesives for bonding and fixing the distal end portion and the proximal end portion to the first rigid portion and the second rigid portion, respectively.

5. The endoscope according to claim 3, wherein the center portion of the covering rubber has predetermined rubber hardness degrees to enable a bending action of the bending portion.

6. The endoscope according to claim 1, wherein a rigid portion of the covering rubber has higher deformation strength in a diameter direction than a flexible portion thereof.

7. The endoscope according to claim 1, wherein a rigid portion of the covering rubber has higher deformation strength in an axial direction than a flexible portion thereof.

8. The endoscope according to claim 1, wherein rubber hardness degrees of the covering rubber at the tightly bound portions is greater than the rubber hardness degrees of the covering rubber at the portion covering the center portion of the bending portion.

9. The endoscope according to claim 1, wherein a rigid portion of the covering rubber has higher deformation strength in a direction around an axis than a flexible portion thereof.

10. The endoscope according to claim 1, wherein the covering rubber is formed by a rubber member with rubber hardness degrees from the distal end to the proximal end having predetermined rubber hardness degrees, and the rubber hardness degrees of the distal end portion and the rubber hardness degrees of the proximal end portion are greater than the rubber hardness degrees of the center portion by immersing a side of the distal end portion and a side of the proximal end portion of the rubber member in cross-linking reagents to raise cross-linking density of the distal end portion and the proximal end portion.

11. The endoscope according to claim 1, wherein the covering rubber is formed by mixing the first thermoplastic elastomer and the second thermoplastic elastomer having different rubber hardness degrees and the rubber hardness degrees of the distal end portion and the rubber hardness degrees of the proximal end portion are greater than the rubber hardness degrees of the center portion by changing mixing amounts of the first thermoplastic elastomer and the second thermoplastic elastomer in the longitudinal direction.

12. The endoscope according to claim 1, wherein the covering rubber is formed by mixing a first thermoplastic elastomer and a second thermoplastic elastomer having different rubber hardness degrees, and the hardness degrees of the distal end portion and the hardness degrees of the proximal end portion are set greater than the hardness degrees of the center portion by changing a mixing ratio of the first elastomer and the second elastomer.

\* \* \* \* \*